(12) United States Patent
Tabet et al.

(10) Patent No.: US 9,616,093 B2
(45) Date of Patent: *Apr. 11, 2017

(54) PLACENTAL MEMBRANE PREPARATION AND METHODS OF MAKING AND USING SAME

(71) Applicant: NuTech Medical, Inc., Birmingham, AL (US)

(72) Inventors: Samuel K. Tabet, Albuquerque, NM (US); Gregory J. Yager, Mount Olive, AL (US); Howard P. Walthall, Jr., Birmingham, AL (US)

(73) Assignee: NuTech Medical, Inc., Birmingham, AL (US)

( * ) Notice: Subject to any disclaimer, the term of this patent is extended or adjusted under 35 U.S.C. 154(b) by 23 days.

This patent is subject to a terminal disclaimer.

(21) Appl. No.: 13/754,742

(22) Filed: Jan. 30, 2013

(65) Prior Publication Data

US 2015/0224147 A1 Aug. 13, 2015

(51) Int. Cl.
*A61K 35/50* (2015.01)
*A61K 35/32* (2015.01)

(52) U.S. Cl.
CPC .............. *A61K 35/50* (2013.01); *A61K 35/32* (2013.01)

(58) Field of Classification Search
CPC .... A61K 2300/00; A61K 35/50; A61K 35/12; A61K 38/57; A61K 35/32; A61F 2/30756
See application file for complete search history.

(56) References Cited

U.S. PATENT DOCUMENTS

| | | | |
|---|---|---|---|
| 4,846,835 A * | 7/1989 | Grande | 128/898 |
| 5,612,028 A * | 3/1997 | Sackier et al. | 424/93.7 |
| 2003/0033021 A1 * | 2/2003 | Plouhar et al. | 623/23.57 |
| 2003/0143207 A1 * | 7/2003 | Livesey et al. | 424/93.7 |
| 2004/0062790 A1 * | 4/2004 | Constantine et al. | 424/426 |
| 2006/0083728 A1 * | 4/2006 | Kusanagi et al. | 424/94.1 |
| 2006/0190017 A1 * | 8/2006 | Cyr et al. | 606/151 |
| 2007/0178158 A1 * | 8/2007 | Knaack et al. | 424/484 |
| 2008/0046095 A1 * | 2/2008 | Daniel | 623/23.74 |
| 2008/0213332 A1 * | 9/2008 | Slavin et al. | 424/423 |
| 2008/0262616 A1 * | 10/2008 | McKay | 623/14.12 |
| 2010/0015102 A1 * | 1/2010 | Iwasaki et al. | 424/93.7 |
| 2011/0206776 A1 * | 8/2011 | Tom | A01N 1/0221 424/583 |
| 2012/0083900 A1 * | 4/2012 | Samaniego | A61L 27/3604 623/23.72 |
| 2013/0230561 A1 * | 9/2013 | Daniel et al. | 424/400 |

OTHER PUBLICATIONS

Li et al. "Human placenta-derived mesenchymal stem cells with silk fibroin biomaterial in the repair of articular cartilage defects." Cell Reprogram. (Aug. 2012);14(4):pp. 334-341.*
Merriam-Webster online dictionary. "Fold." http://www.learnersdictionary.com/definition/fold. accessed Jul. 14, 2014.*
Dahlberg, L. and Kreicbergs, "Demineralized allogeneic bone matrix for cartilage repair." (1991) J. Orthop. Res., 9:11-19.*

* cited by examiner

*Primary Examiner* — Titilayo Moloye
(74) *Attorney, Agent, or Firm* — C. Brandon Browning; Maynard, Cooper & Gale, PC

(57) ABSTRACT

This disclosure relates to placental membrane preparations and the methods of preparing and using thereof. In some embodiments, the disclosure relates to a placental membrane preparation. In some embodiments, the disclosure relates to methods of producing a placental membrane preparation. In some embodiments, the disclosure relates to methods of treating cartilage using placental membrane preparations.

27 Claims, 10 Drawing Sheets

PLACENTAL MEMBRANE PREPARATION AND METHODS OF MAKING AND USING SAME

FIELD OF THE INVENTION

The present invention is directed to a placental membrane preparation. More particularly, the present invention is directed to a placental membrane preparation and methods of making and using same.

BACKGROUND OF THE INVENTION

The placenta surrounds a fetus during gestation and is composed of, among other tissues, an inner amniotic layer that faces the fetus and a generally-inelastic outer shell, or chorion. The placenta anchors the fetus to the uterine wall, allowing nutrient uptake, waste elimination, and gas exchange to occur via the mother's blood supply. Additionally, the placenta protects the fetus from an immune response from the mother. From the placenta, an intact placental membrane comprising the amnion and chorion layers can be separated from the other tissues.

Clinicians have used intact placental membrane, comprising an amnion and a chorion layer, in medical procedures since as early as 1910 [Davis, J. S., *John Hopkins Med. J.* 15, 307 (1910)]. The amniotic membrane, when separated from the intact placental membrane, may also be used for its beneficial clinical properties [Niknejad H, et al. *Eur Cell Mater* 15, 88-99 (2008)]. Certain characteristics of the placental membrane make it attractive for use by the medical community. These characteristics include, but are not limited to, its anti-adhesive, anti-microbial, and anti-inflammatory properties; wound protection; ability to induce epithelialization; and pain reduction. [Mermet I, et al. *Wound Repair and Regeneration,* 15:459 (2007)].

Other uses for placental membrane include its use for scaffolding or providing structure for the regrowth of cells and tissue. An important advantage of placental membrane in scaffolding is that the amnion contains an epithelial layer. The epithelial cells derived from this layer are multipotent cells, allowing the cells to multiply and differentiate into cells of other types. Multipotent cells are also contained within the body of the amniotic membrane. Additionally, the amniotic membrane contains various growth and trophic factors, such as epidermal, insulin-like, and fibroblast growth factors, as well as high concentrations of hyaluronic acid, that may be beneficial to prevent scarring and inflammation and to support healing. Thus, placental membrane offers a wide variety of beneficial medical uses.

Cell-based therapies have considerable potential for the repair and regeneration of tissues. The addition of a scaffold to these cell-based therapies has yielded improved outcomes [Krishnamurithy G, et al. *J Biomed Mater Res Part A* 99A, 500-506 (2011)]. Ideally, the material used for the scaffold will be biocompatible such that it provokes little to no immune response, biodegrades, and is available in sufficient quantities to be practical. Although the placental membrane has long been identified as a materially potentially filling this role in the clinic, efforts have been limited to in vitro studies, impractical in vivo techniques, or have yielded less than optimal outcomes. Furthermore, the conditions under which the scaffold is used may have a dramatic effect on the therapeutic efficacy.

Multiple studies exist expounding on the potential uses of human amniotic cells in various platforms for tissue repair. It has been proven that amniotic cells are multipotent in nature and can be influenced to produce various cell lines including chondrocytes. Further, it has been shown in the lab that demineralized bone can influence multipotent cells to produce both chondrocyte and osteoblast type cells.

Articular cartilage, located on the articular ends of bones at joints throughout the body, is composed of hyaline cartilage and contains relatively few chondrocytes that are embedded in extracellular matrix materials, such as type II collagen and proteoglycan [Moriya T, et al. *J Orthop Sci* 12, 265-273 (2007)]. Articular cartilage has a limited ability to self-repair, in part due to the avascular characteristics of the cartilage, which poses a significant challenge to treating joint injuries or diseases. The repair of cartilage defects in humans can therefore be a difficult endeavor, and multiple options exist for the surgeon to approach this topic. The surgeon may choose to influence the defect with microfracture of abrasion techniques to stimulate bleeding and a resulting fibrocartilage patch in which to fill the defect. There are also options available that allow for the filling of the defect with chondrocytes of variable sources, both of autograft and allograft origin.

However, current treatments, including cell-based therapies, have resulted in the generation of undesirable fibro-cartilaginous tissue rather than hyaline cartilage [Diaz-Prado S M, et al. BIOMEDICAL ENGINEERING, TRENDS, RESEARCH, AND TECHNOLOGIES, pp. 193-216 (2011)]. As such, there remains a significant clinical need for therapies capable of repairing damaged articular cartilage that are capable of regenerating hyaline cartilage.

SUMMARY OF THE INVENTION

The present invention is directed to a placental membrane preparation and methods of making and using same. In some embodiments, the invention is directed to a placental membrane preparation including demineralized bone powder and a placental membrane sheet. The chorion layer may be excluded from the placental membrane sheet. DBP may be applied to a stromal layer of the placental membrane sheet. The DBP may be reconstituted. The placental membrane sheet may be folded to form an implantable unit. A portion of the amnion side of the implantable unit may be exposed. The amnion side of the placental membrane sheet may be covered with a layer of placental epithelial cells. The chorion side of the placental membrane sheet may include a stromal surface layer. The placental membrane preparation may or may not include chondrocytes. The chondrocytes may be derived from autologous or allograft chondrocytes or multipotent cells originating from the placental membrane sheet. The placental membrane sheet may include viable placental membrane cells.

In another embodiment, the invention is directed to a method of making a placental membrane preparation including applying a demineralized bone powder to a placental membrane sheet. The DBP, which may be reconstituted, may be applied to a stromal layer of the placental membrane sheet. The chorion layer may be removed prior to applying DBP. The placental membrane sheet may be essentially free of chondrocytes prior to implantation into a patient since chondrogenic differentiation of the placental membrane cells may occur in vivo. Chondrogenic differentiation may be induced in a plurality of multipotent cells of the placental membrane sheet. This differentiation may be induced in an essentially oxygen-free environment or in the absence of blood components. The placental membrane sheet may be dried, rehydrated, and DBP may be applied before, during, or after rehydration of the placental membrane sheet. An implantable unit may be formed by folding the placental membrane sheet.

In another embodiment, the invention is directed to a method of generating cartilage in vivo in a skeletal joint, the method including implanting a placental membrane preparation, as described herein, into the skeletal joint wherein the placental membrane preparation comprises a placental membrane sheet and a demineralized bone powder applied thereto. The cartilage that is generated may comprise, in whole or part, hyaline articular cartilage. The method of generating cartilage in vivo may comprise placing a patch over the preparation and suturing the patch to the skeletal joint.

In another embodiment, the invention is directed to a method of generating cartilage in vivo in a skeletal joint, the method including removing a diseased cartilage portion from a cartilage body of the skeletal joint, wherein the leakage of blood caused by removing the diseased cartilage portion is minimized, and essentially all of the blood from the skeletal joint is removed prior to implantation of a placental membrane sheet into the skeletal joint. The diseased cartilage may be removed in a manner that leaves sustainably all of the healthy cartilage intact. Removing the diseased cartilage portion may expose an underlying bone. The underlying bone may be intact. The underlying bone may be leaking blood, which, along with any blood clots, may be removed. A layer of bone wax may be applied to any void caused by the removal of diseased or damaged cartilage from the skeletal joint. A placental membrane sheet, with or without DBP, may be implanted into a void formed in the cartilage body caused by removal of diseased cartilage.

In another embodiment, the invention is directed to a method of generating cartilage in vivo in a skeletal joint, the method including providing an insert including a placental membrane sheet and a collagen matrix that may contain one or more growth factors, and implanting the insert into the skeletal joint. The growth factor may be DBP. The implant may be inserted without disturbing any calcified cartilage therein. The insert may have an epithelial layer such that the epithelial layer makes up at least 90% of the insert's exterior. The insert may be positioned such that the insert includes an epithelial layer having a first portion facing toward a skeletal joint bone and a second portion facing away from the skeletal joint bone. A layer of bone wax may be applied to any void caused by the removal of diseased or damaged cartilage from the skeletal joint. The diseased or damaged cartilage may be removed without perforating subchondral bone. An epithelial layer of the placental membrane may be applied to the walls of the void.

A further understanding of the nature and advantages of the present invention will be realized by reference to the remaining portions of the specification and the drawings of the present application.

DETAILED DESCRIPTION OF THE INVENTION

Figure 1:
FIG. 1 is a top plan view of a placental membrane sheet in accordance with a preferred embodiment of the present invention.

Before the present compositions, articles, devices, and/or methods are disclosed and described, it is to be understood that they are not limited to specific methods unless otherwise specified, or to particular reagents unless otherwise specified, and as such may vary. It is also to be understood that the terminology as used herein is used only for the purpose of describing particular embodiments and is not intended to be limiting.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

A. Definitions

In this specification, and in the claims that follow, reference is made to a number of terms that shall be defined to have the following meanings:

As used herein, the singular forms "a," "an," and "the" include plural referents unless the context clearly indicates otherwise. Thus, for example, reference to "a pharmaceutical carrier" includes mixtures of two or more such carriers, and the like.

As used herein, ranges can be expressed as from "about" one particular value, and/or to "about" another particular value. When such a range is expressed, an embodiment includes from the one particular value and/or to the other particular value. Similarly, when values are expressed as approximations, by the use of "about," it will be understood that the particular value forms another embodiment. It will be understood that the endpoints of each of the ranges are significant both in relation to the other endpoint and independently of the other endpoint. It will also be also understood that there are a number of values disclosed herein, and that each value is also disclosed herein as "about" that particular value in addition to the value itself. For example, if the value "50" is disclosed, then "about 50" is also disclosed. It is also understood that when a value is disclosed that "less than or equal to" a value, that values "greater than or equal to the value" and possible ranges between values are also disclosed, as understood by one skilled in the art. For example, if the value "50" is disclosed, then "less than or equal to 50" and "greater than or equal to 50" are also disclosed. It is also understood that the throughout the application, data are provided in different formats, and it is understood that these data represent endpoints and starting points as well as ranges for any combination of the data points. For example, if a particular data point "50" and a particular data point "100" are disclosed, it is understood that greater than, greater than or equal to, less than, less than or equal to, and equal to 50 and 100 are considered disclosed as well as between 50 and 100.

As used herein, the terms "optional" or "optionally" mean that the subsequently described event or circumstance may or may not occur, and that the description includes instances where said event or circumstance occurs and instances where it does not occur.

As used herein, the phrase "essentially oxygen-free environment" refers to an environment in which the free oxygen content is less than that of normal air, for example in an within articular cartilage. The term "free oxygen" refers to oxygen that is not combined with one or more other elements. Similarly, the phrase "essentially free of chondrocytes" refers to a composition which does not natively contain chondrocytes, and to which no extraneous chondrocytes have been added. For example, a placental membrane sheet that is essentially free of chondrocytes is a placental membrane sheet in which chondrocytes are not seeded onto the membrane.

As used herein, the phrase "essentially all chondrocytes" refers to a majority of the chondrocytes. Preferably, this refers to the maximum percentage of chondrocytes that can be reasonably attained by one of skill in the art. For example, where essentially all of the chondrocytes are derived from a particular source, other sources of chondrocytes may be excluded, inhibited, or reduced.

As used herein, the phrase "substantially all" refers to the maximum amount reasonably attainable by one skilled in the art. For example, removing diseased cartilage from a knee joint that leaves "sustainably all healthy portions of the cartilage body" indicates the removal of diseased cartilage that removes as little healthy cartilage as reasonably possible by one skilled in the art, such as a surgeon.

As used herein, the phrase "diseased cartilage" refers to cartilage that is damaged, degenerating, inflamed, necrotic, or otherwise showing symptoms thereof, such as pain, swelling, stiffness, and restraint of movement. Diseased cartilage may be diagnosed in several ways including, but not limited to, x-ray analysis, MRI analysis, or arthroscopy.

As used herein, the phrase "calcified cartilage" refers to the zone of cartilage that connects articular cartilage to the underlying subchondral bone.

As used herein, the phrase "bone wax" refers to a hemostatic material used to control bleeding from the surface of bone. For example, bone wax may be comprised of beeswax. In another example, bone wax comprises beeswax and one or more softening agents, such as paraffin. In another example, bone wax may comprise other inert hemostatic compounds, such as alkylene oxide copolymers.

As used herein, the phrases "placental membrane sheet" or "placental membrane" refer to one or more layers of the placental membrane. For example, placental membrane sheet may refer to a placental membrane comprising both the amniotic and chorionic layers. In another example, placental membrane sheet may refer to a placental membrane in which the chorion has been removed. In another example, placental membrane sheet may refer to a placental membrane in which the epithelial layer has been removed.

As used herein, the phrase "implantable unit" or "implant" refers to a mechanical configuration of a composition, comprising a placental membrane sheet, such that the composition is capable of insertion into or covering a surgical site. For example, an implantable unit may be a composition, comprising a placental membrane sheet, such that the composition is folded to permit insertion of the composition into a skeletal joint, such as the knee or shoulder, during surgery. In another example, an implantable unit may be a composition, comprising a placental membrane sheet, such that the composition is folded to permit covering a portion or an entirety of a skeletal joint during surgery.

As used herein, the term "patch" refers to a biocompatible composition. For example, a patch may comprise a placental membrane sheet. In another example, a patch comprises a portion of amnion.

As used herein, the phrase "subchondral bone" refers to bone underlying cartilage. Subchondral bone may or may not be attached to the cartilage.

As used herein, the phrase "skeletal joint bone" refers to a bone in contact, or associated, with a skeletal joint. For example, a skeletal joint bone associated with the knee joint may include the femur.

As used herein, the phrase "demineralized bone powder" or "DBP" refers to a demineralized bone composition comprised of bone particles. DBP compositions may comprise fine powders, coarse grains, or even chips and are well known to those skilled in the art [Zhou S, et al. *Cell Tissue Bank* 6, 33-44 (2005)].

As used herein, the phrase "chondrogenic differentiation" refers to the differentiation of one cell type into a chondrocyte or chondrocyte-like cell. For example, mesenchymal stem cells may undergo chondrogenic differentiation such that they differentiate into chondrocytes.

As used herein, the phrase "reconstituted DBP" refers to DBP to which a compatible solvent has been added.

As used herein, the terms "treatment" or "treating" include any desirable effect on the symptoms or pathology of a disease or condition, and may include even minimal reductions in one or more measurable markers of the disease or condition being treated. "Treatment" does not necessarily indicate complete eradication or cure of the disease or condition, or associated symptoms thereof. The subject receiving this treatment is any animal in need, including primates, in particular humans, and other mammals including, but not limited to, equines, cattle, swine, and sheep; and poultry and pets in general.

B. Methods of Making Placental Membrane Preparation

FIG. 1 depicts a general shape of placental membrane sheet 100 in accordance with a preferred embodiment of the present invention. Placental membrane sheet 100 is of the type of membrane that is commonly used by clinicians in wound healing, cell regeneration, and tissue grafting applications.

Figure 2:
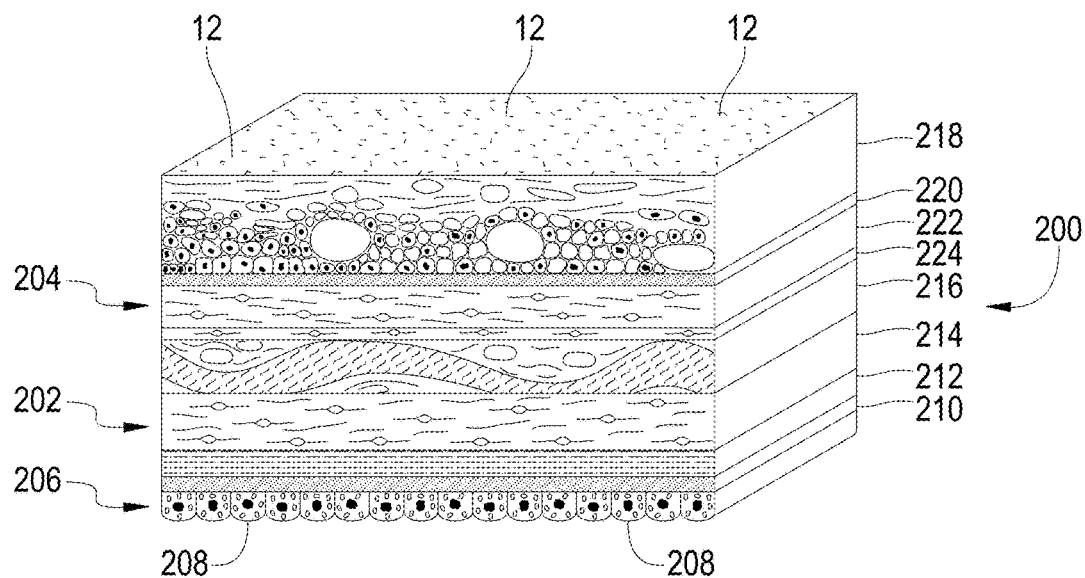
FIG. 2 is a sectional view of a placental membrane sheet in accordance with a preferred embodiment of the present invention.

FIG. 2 depicts an intact placental membrane sheet 200 including an amount of DBP 12 in accordance with a preferred embodiment of the present invention. Intact placental membrane 200 includes an amnion 202 and a chorion 204. Amnion 202 includes an epithelium 206 composed of a monolayer of epithelial cells 208, a basement membrane 210, a compact stromal layer 212, fibroblast layer 214 containing mesenchymal cells and a spongy layer 216. Chorion 204 includes a trophoblast layer 218, a basement membrane 220, a reticular layer 222 and a cellular layer 224. As illustrated, DBP 12 is applied to trophoblast layer 218.

Figure 3:
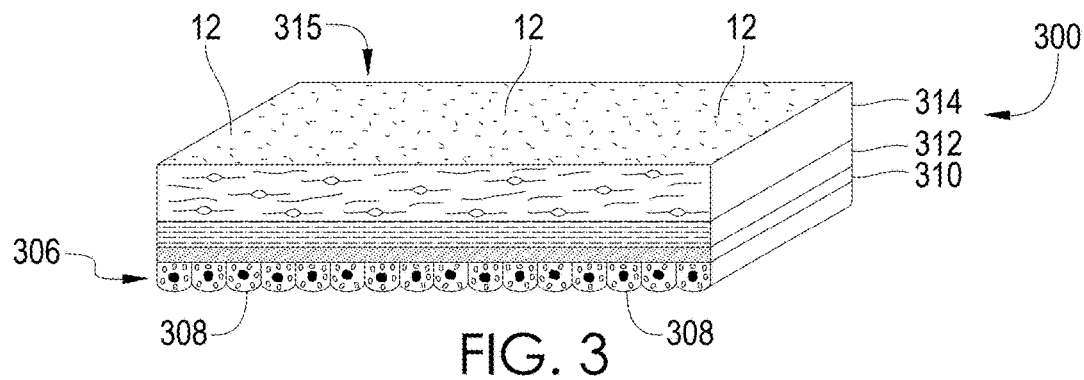
FIG. 3 is a sectional view of a placental membrane sheet in accordance with a preferred embodiment of the present invention.

FIG. 3 depicts a placental membrane sheet 300 including an amount of DBP 12 in accordance with another preferred embodiment of the present invention. Placental membrane 300 includes an amnion with the chorion removed, an amnion side 313 and a chorion side 315. Amnion includes an epithelium 306 composed of a monolayer of epithelial cells 308, a basement membrane 310, a compact stromal layer 312, and a fibroblast layer 314 containing mesenchymal cells. As illustrated, DBP 12 is applied to fibroblast layer 314. However, it is anticipated that removal of the chorion from placental membrane 300 will expose stromal layer 312 so that DBP 12 may be applied directly to stromal layer 312.

1. Initial Treatment and Removal of Particular Layers of the Placental Membrane

Placental membrane sheets 100, 200 and 300, depicted in FIGS. 1-3, and similar placental membrane materials may be produced from placentas collected from consenting donors in accordance with the Current Good Tissue Practice guidelines promulgated by the U.S. Food and Drug Administration.

In particular, soon after the birth of a human infant via a Cesarean section delivery, the intact placenta is retrieved, and the placental membrane is dissected from the placenta. Afterwards, the placental membrane is cleaned of residual blood, placed in a bath of sterile solution, stored on ice and shipped for processing. Once received by the processor, the placental membrane is rinsed to remove any remaining blood clots, and if desired, rinsed further in an antibiotic rinse [Diaz-Prado S M, et al. *Cell Tissue Bank* 11, 183-195 (2010)].

The antibiotic rinse may include, but is not limited to, the antibiotics: amikacin, aminoglycosides, amoxicillin, ampicillin, ansamycins, arsphenamine, azithromycin, azlocillin, aztreonam, bacitracin, capreomycin, carbacephem, carbapenems, carbenicillin, cefaclor, cefadroxil, cefalexin, cefalotin, cefamandole, cefazolin, cefdinir, cefditoren, cefepime, cefixime, cefoperazone, cefotaxime, cefoxitin, cefpodoxime, cefprozil, ceftaroline fosamil, ceftazidime, ceftibuten, ceftizoxime, ceftobiprole, ceftriaxone, cefuroxime, chloramphenicol, ciprofloxacin, clarithromycin, clindamycin, clofazimine, cloxacillin, colistin, cycloserine, dapsone, daptomycin, demeclocycline, dicloxacillin, dirithromycin, doripenem, doxycycline, enoxacin, ertapenem, erythromycin, ethambutol, ethionamide, flucloxacillin, fosfomycin, furazolidone, fusidic acid, gatifloxacin, geldanamycin, gentamicin, glycopeptides, grepafloxacin, herbimycin, imipenem or cilastatin, isoniazid, kanamycin, levofloxacin, lincomycin, lincosamides, linezolid, lipopeptide, lomefloxacin, loracarbef, macrolides, mafenide, meropenem, methicillin, metronidazole, mezlocillin, minocycline, monobactams, moxifloxacin, mupirocin, nafcillin, nalidixic acid, neomycin, netilmicin, nitrofurans, nitrofurantoin, norfloxacin, ofloxacin, oxacillin, oxytetracycline, paromomycin, penicillin G, penicillin V, piperacillin, platensimycin, polymyxin B, pyrazinamide, quinolones, quinupristin/dalfopristin, rifabutin, rifampicin or rifampin, rifapentine, rifaximin, roxithromycin, silver sulfadiazine, sparfloxacin, spectinomycin, spiramycin, streptomycin, sulfacetamide, sulfadiazine, sulfamethizole, sulfamethoxazole, sulfanilamide, sulfasalazine, sulfisoxazole, sulfonamidochrysoidine, teicoplanin, telavancin, telithromycin, temafloxacin, temocillin, tetracycline, thiamphenicol, ticarcillin, tigecycline, tinidazole, tobramycin, trimethoprim, trimethoprim-sulfamethoxazole (co-trimoxazole) (TMP-SMX), troleandomycin, trovafloxacin, or vancomycin.

The antibiotic rinse may also include, but is not limited to, the antimycotics: abafungin, albaconazole, amorolfin, amphotericin B, anidulafungin, bifonazole, butenafine, butoconazole, caspofungin, clotrimazole, econazole, fenticonazole, fluconazole, isavuconazole, isoconazole, itraconazole, ketoconazole, micafungin, miconazole, naftifine, nystatin, omoconazole, oxiconazole, posaconazole, ravuconazole, sertaconazole, sulconazole, terbinafine, terconazole, tioconazole, voriconazole, or other agents or compounds with one or more anti-fungal characteristics.

The placental membrane may be processed to remove one or more particular layers of the membrane. The chorion may be removed from the placental membrane by mechanical means well-known to those skilled in the art. The chorion may be removed, for example, by carefully peeling the chorion from the remainder of the placental membrane using blunt dissection [Jin C Z, et al. *Tiss Eng* 13, 693-702 (2007)]. Removal of the epithelial layer from the placental membrane may be achieved using several methods well-known to those skilled in the art. The epithelial layer may be removed by, for example, using trypsin to induce necrosis in the epithelial cells [Diaz-Prado S M, et al. *Cell Tissue Bank* 11, 183-195 (2010)]. Removal of the epithelial layer may comprise, for example, treatment with 0.1% trypsin-ethylenediaminetetraacetic acid (EDTA) solution at 37C for 15 minutes followed by physical removal using a cell scraper [Jin C Z, et al. *Tiss Eng* 13, 693-702 (2007)].

The placental membrane may then be stored in packs containing a sterile solution, air dried, or freeze dried. Both air drying and freeze drying are well known to those skilled in the art [Boo L, et al. *Malay Orthop J* 3, 16-23 (2009)]. The placental membrane may be air dried, for example, by spreading the membrane under a laminar flow or bio-safety hood, or like environment wherein the possibility of contamination is reduced, until dry. Typically, the placental membrane may be air dried overnight, typically for approximately 6 hours or more or preferably for 12 hours or more. The placental membrane may be freeze dried, for example, by placing the stretched placental membrane into a plastic bag in a freeze drier until dry. The placental membrane may be frozen prior to transfer to a freeze drier. Typically, the placental membrane may be freeze dried for approximately 6 hours or more or preferably for 12 hours or more. If the placental membrane is stored in a sterile solution, it may be stored at room temperature, cold stored at refrigerator temperatures, or cryopreserved at a temperature bellowing the freezing temperature of the solution.

The placental membrane preparation may be sterilized, typically using irradiation, as is well-known to those skilled in the art. Approximately 25 kGy gamma irradiation, for example, may be used for sterilization of the placental membrane preparation [Krishnamurithy G, et al. *J. Biomed Mater Res Part A* 99A, 500-506 (2011)]. The placental membrane may be rehydrated using, for example, a sterile buffered saline solution [U.S. Patent Application Publication No. 2003-0187515].

Figure 4:
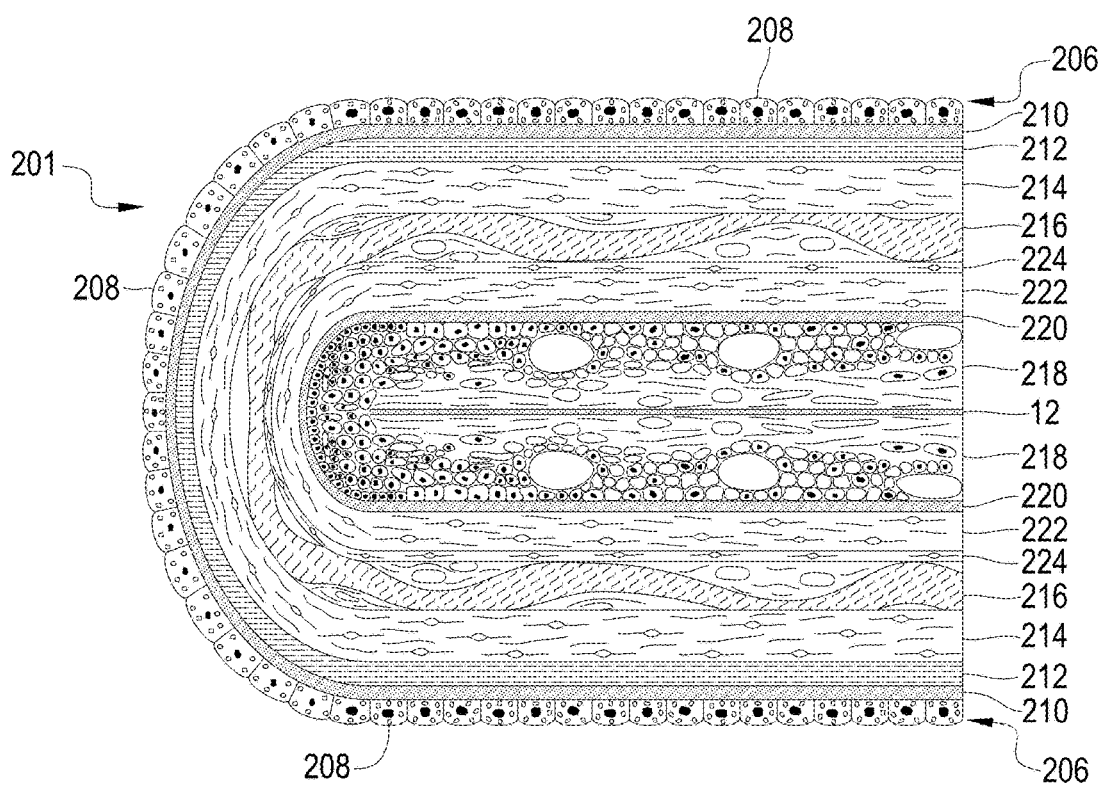
FIG. 4 is a sectional view of a placental membrane implant prepared using the placental membrane sheet of FIG. 2.
Figure 5:
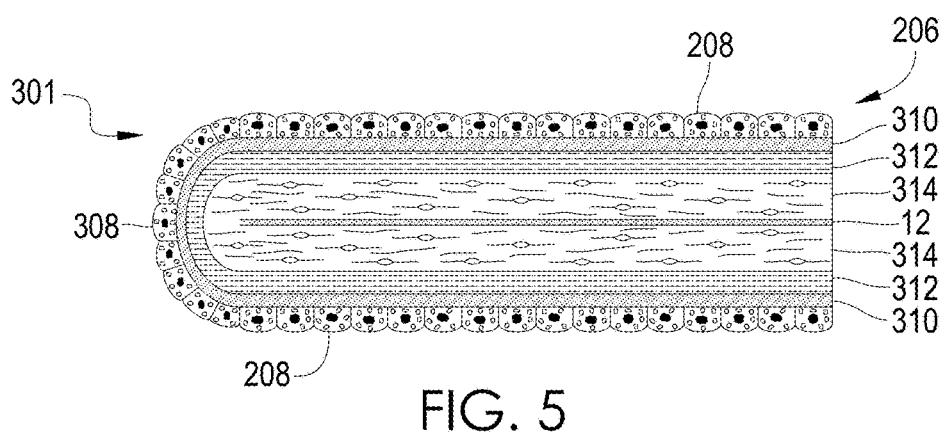
FIG. 5 is a sectional view of a placental membrane implant prepared using the placental membrane sheet of FIG. 3.

Referring to FIGS. 4 and 5, placental membrane sheets 200 and 300 may be folded to form implantable units 201 and 301, respectively. One or more folds may be created in the placental membrane sheet to permit the placental membrane preparation to fit or be in the proper orientation at the target site in vivo. The placental membrane sheet may be folded, for example, in a manner that exposes an epithelial layer that may then be inserted such that the epithelial layer is in direct contact with cartilage. In addition, the folds may be created to expose a particular percentage of the placental membrane sheet's surface area as part of the implantable unit. Folds may also be created in the placental membrane sheet to expose a particular side or layer, such as amniotic or epithelial, of the placental membrane preparation.

The placental membrane sheet may be combined with a collagen matrix. A collagen matrix is a three-dimensional scaffold comprising one or more forms of collagen including, but not limited to, for example, type I collagen, type II collagen, and type IV collagen. In addition, the collagen matrix may include one or more growth factors including, but not limited to, for example, TGF-β. A collagen matrix may be prepared using a variety of methodologies well-known to those skilled in the art. For example, a porous collagen matrix may be created by using pepsin-digested bovine collagen that is neutralized with 1 M HEPES at pH 7.4, 1 M NaH—$CO_3$, poured into a mold, frozen, lyophilized, and then irradiated [Zhou S, et al. *Cell Tissue Bank* 6, 33-44 (2005)].

2. Chondrocyte Differentiation

In vitro laboratory studies have indicated that chondrogenic differentiation may be induced in multiple cell types by the application of DBP under the appropriate culture conditions. Chondrogenesis may be induced in, for example, human dermal fibroblasts or human marrow stromal cells (hMSCs) using DBP and chondrogenic medium in combination with a collagen sponge system [Zhou S, et al. *Cell Tissue Bank* 6, 33-44 (2005)]. However, in this system under other culture conditions differentiation into osteoblasts may also result from the application of DBP. In fact, demineralized bone products are currently in surgical use primarily for the stimulation of bone growth. In the context of a diseased joint, the growth of bone spurs or other ectopic bone growth is not desirable and would likely cause a worsening of the condition of the joint The differentiation of multiple cells types, such as mesenchymal stem cells, into chondrocytes may also be significantly affected by the presence or absence of growth factors. In the formation of cartilage, for example, TGF-β has been shown to have a substantial role [Hildner F, et al. *J Tissue Eng Regen Med* 5, e36-e51 (2011)]. In the placental membrane, the epithelial layer is a source of several growth factors including, but not limited to, EGF, KGF, HGF, and bFGF [Niknejad H, et al. *Eur Cell Mater* 15, 88-99 (2008)]. The epithelial layer also includes cytokines, such as activin, NGF, noggin, and TNF-α, that may play a role in cell differentiation. If the epithelial layer is removed from the placental membrane, as described herein, it is possible to seed the resulting membrane with epithelial or mesenchymal stem cells from the particular patient to avoid inducing or mitigating an immune response that may otherwise occur with allogeneic cells. Alternatively, exogenous growth factors may be introduced to induce the differentiation of placental membrane cells or of cells seeded thereon.

For the placental membrane preparation, chondrocytes may be derived from particular cell types. Chondrocytes may be derived from particular cell types by, for example, isolating that cell type, culturing, and differentiating either in vitro or in vivo. Particular cell types may be isolated using a variety of techniques well-known to those skilled in the art including, but not limited to, adherence to tissue culture plates or separation via cell sorting devices (e.g. autoMACS® Pro Separator, Miltenyi Biotec). The purity of a particular cell type within the pool of isolated cells may be tested using, for example, flow cytometry by which a distinctive set of surface or intracellular markers may be analyzed to ensure purity. The purity of a particular cell type within the pool of isolated cells may be tested using, for example, morphological analysis via microscopy. Both flow cytometry and morphological analysis via microscopy are well-known to those skilled in the art.

Cell viability may be assessed using a variety of techniques well-known to those skilled in the art including, but not limited to, flow cytometry or morphological analysis via microscopy. Flow cytometry using, for example, antibodies specific for annexin-V and propidium iodide will indicate cells that are apoptotic or necrotic, respectively.

The placental membrane sheet may be seeded using a variety of cell types. Isolated autologous or allograft chondrocytes, for example, may be seeded onto the placental membrane sheet in vitro. Similarly, other cell types, such as mesenchymal stem cells, may be seeded and subsequently differentiated into chondrocytes, either in vitro or in vivo, as described herein. In addition, placental membrane cells may be differentiated into chondrocytes. Unexpectedly, the in vitro application of placental membrane and DBM under the conditions described herein results in the growth and differentiation of chondrocyte-like cells, without differentiation of cells into osteoblasts resulting in ectopic bone growth.

C. Uses of the Placental Membrane Preparation

The embodiments of the placental membrane preparation, described herein, may be used to regenerate damaged or defective tissue. Preferably, the embodiments of the placental membrane preparation, described herein, may be used to regenerate hyaline articular cartilage in vivo, with essentially no fibrocartilage generation and without the growth of bone spurs or other ectopic bone growth. The compositions and methods pertaining to the placental membrane preparation may be used in a number of clinical conditions including, but not limited to, chondral defects, osteoarthritis, traumatic injury, such as rotational or compaction injuries, osteochondritis dessicans, pathological injury, age-related degeneration, and other defects affecting skeletal joints, in particular cartilage.

Figure 6:
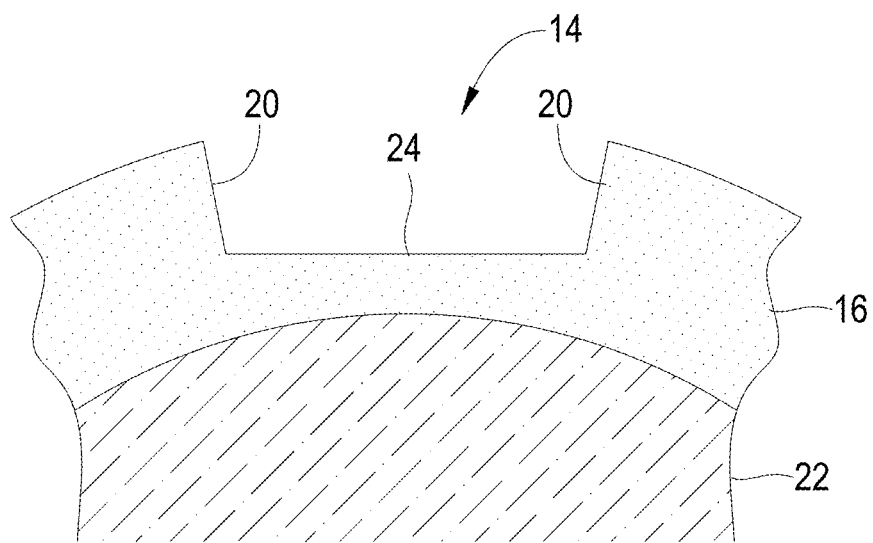
FIG. 6 is a sectional view of an articular joint depicting a void created in accordance with a preferred embodiment of the present invention.
Figure 7:
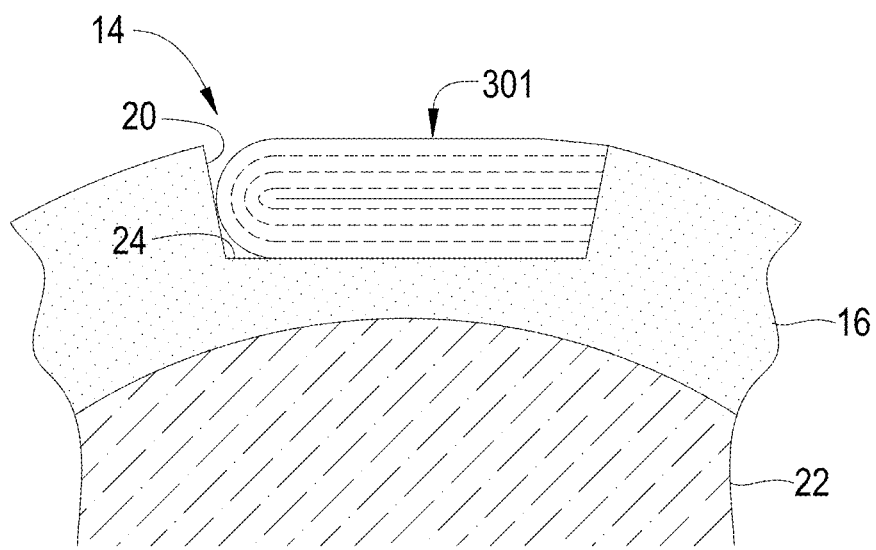
FIG. 7 is sectional view of the articular joint of FIG. 6 including the placental membrane implant of FIG. 4.

Referring to FIGS. 6 and 7, a placental membrane preparation such as implantable unit 301 may be implanted into a particular site in vivo, such as a skeletal joint, using surgical techniques well-known to those skilled in the art. The placental membrane preparation may be implanted, for example, into a void 14 in the articular cartilage 16 in a skeletal joint for the purpose of regenerating hyaline articular cartilage within void 14. Void 14 includes a sidewall 20 of cartilage, an upper opening and a bottom 24. Preferably, bottom 24 is composed of cartilage since it is desired to minimize bleeding and leave subchondral bone 22 undisturbed. Preferably, the placental membrane preparation substantially fills void 14.

Figure 8:
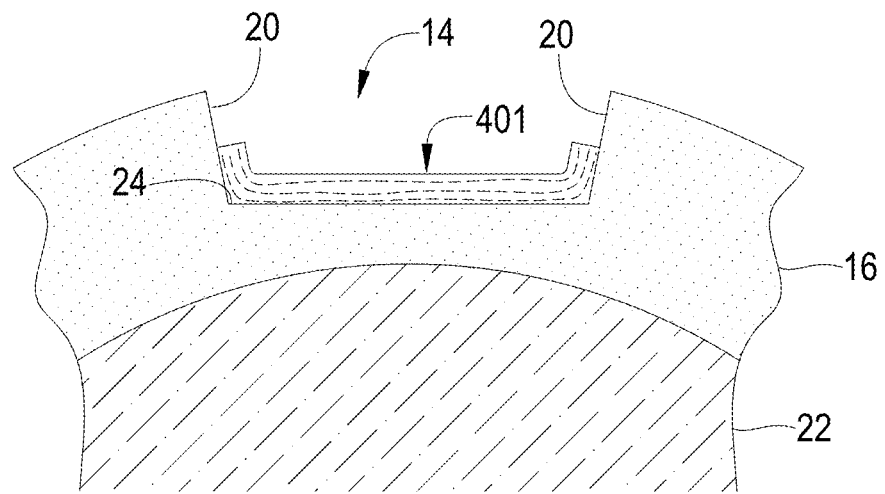
FIG. 8 is a sectional view of the articular joint of FIG. 6 including the placental membrane implant of FIG. 3.
Figure 9:
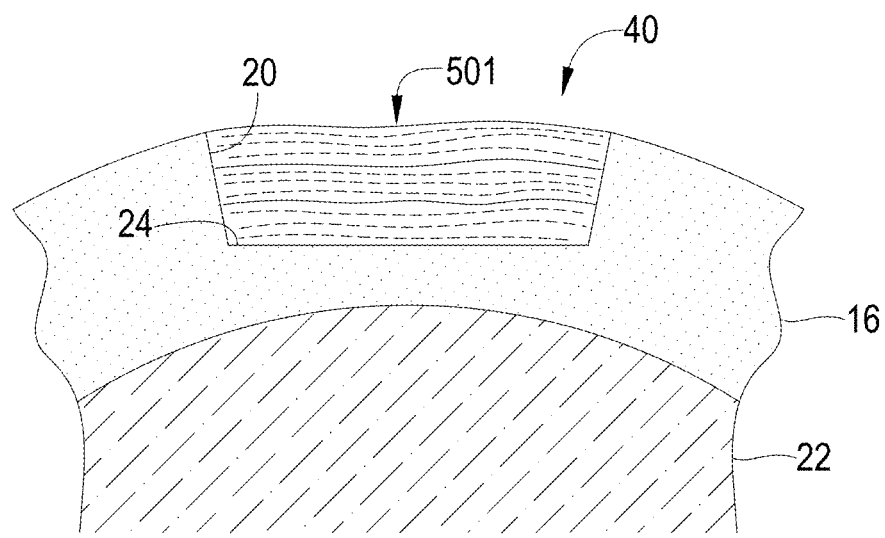
FIG. 9 is a sectional view of the articular joint of FIG. 6 including multiple unfolded placental membrane implantable units.

As an alternative to folded, implantable units 201 and 301, it is anticipated that the placental membrane preparations may be implanted into a skeletal joint in various unfolded orientations. For example, as depicted in FIG. 8, a placental membrane preparation may be presented as an implantable unit 401 having the amnion or epithelial side of unit 401 facing bottom 24 and the chorion side, impregnated with DBP, facing the upper opening. In this embodiment, implantable unit 401 is provided as a single, unfolded placental membrane layer covering bottom 24 of void 14, and optionally a portion of sidewall 20. Additionally, as depicted in FIG. 9, the placental membrane preparation may be presented as an implantable unit 501 composed of multiple, unfolded placental membrane layers stacked on top of one another. In this embodiment, the bottommost layer is preferably oriented with the amnion or epithelial side facing and covering bottom 24 with the topmost placental membrane layer oriented with its amnion or epithelial side facing the upper opening. The intermediate placental membrane layers can be oriented in whatever manner is deemed most advantageous. In this embodiment, DBP is applied to the chorion side of one or more of the placental membrane layers. Preferably, placental membrane layers of unit 501 are stacked within void 14 so that the upper surface of implantable unit 501 lies immediately below a plane formed by the upper opening.

Prior to implantation of the placental membrane preparation, the subchondral bone may inadvertently be perforated or abrasions formed. Perforations or abrasions in the subchondral bone or the calcified cartilage may induce bleeding and the formation of a fibrous clot in the defect, as well as the subsequent invasion of mesenchymal progenitor cells from the bone marrow to the site of the damaged cartilage. For this reason cartilage repair procedures currently in use such as microfracture intentionally perforate the subchondral bone in order to induce clotting and initiate repair. However, introduction of blood and/or mesenchymal progenitor cells from the bone marrow into the void may induce the formation of fibrocartilage in place of the desired hyaline cartilage. Accordingly, in the claimed technique the leakage of blood should be minimzed, and any blood clots that may form as a result of the blood leakage should be removed. Techniques for the removal of blood and blood clots are well-known to those skilled in the art. Such techniques may include, but are not limited to, for example, aspiration. Hemostatic agents including, but not limited to, bone wax may also be applied to the site of blood leakage, typically exposed subchondral bone.

Bone marrow may also be released from the subchondral bone, during or proximal to the implantation of the placental membrane preparation. The bone marrow may be removed using techniques well-known to those skilled in the art. Techniques include, but are not limited to, aspiration.

To further prevent formation of fibrocartilage cells from cells derived from the placental membrane sheets, the sheets are folded and arranged within the joint so that the largely impermeable, epithelial cell monolayer of the amnion forms the exterior of the implantable unit. In this way, blood that may collect within a void formed in a joint is separated or shielded from the interior of the implantable unit where chondrogenic growth and differentiation occurs in contact with cartilage on the lateral sides of the graft. By preventing the leakage of blood into the implantable unit, it is believed the mechanisms which cause fibrocartilage and osteoblast formation are substantially reduced or terminated.

D. Example

The following example is presented to provide those of ordinary skill in the art with a complete disclosure and a description of how the compounds, compositions, and methods described and claimed herein are made and evaluated. The following examples are intended to be purely exemplary and are not intended to limit the scope of what the inventors regard as their invention. There are numerous variations and combinations of conditions, e.g., component concentrations, desired solvents, solvent mixtures, temperatures, pressures and other reaction ranges and conditions that can be used to optimize the product from the described process. Only reasonable and routine experimentation will be required to optimize such process conditions. As will be understood by those familiar with the art, the present invention may be embodied in other specific forms without departing from the spirit or essential characteristics thereof.

1. In Vivo Cartilage Repair Trial

A study was performed for evaluating the use of human amniotic membrane mixed with demineralized bone to fill cartilage defects in a sheep model. It was hypothesized that this membrane would be able to fill these defects with chondrocyte-like cells and that the defects would be filled with hyaline cartilage.

Figure 10:
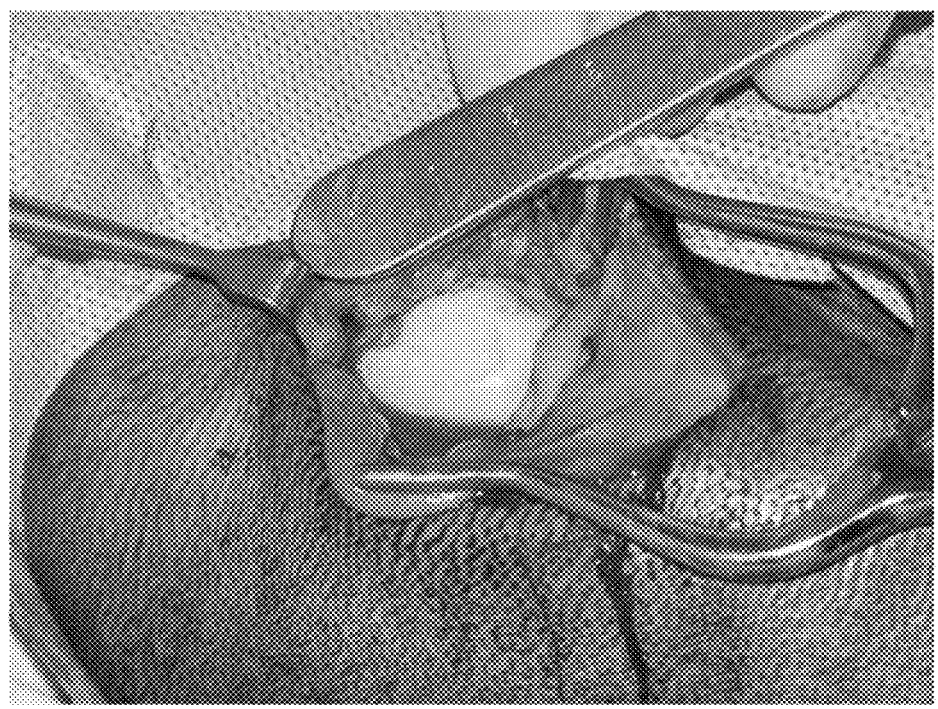
FIG. 10 depicts a cartilage defect in a sheep knee.
Figure 11:
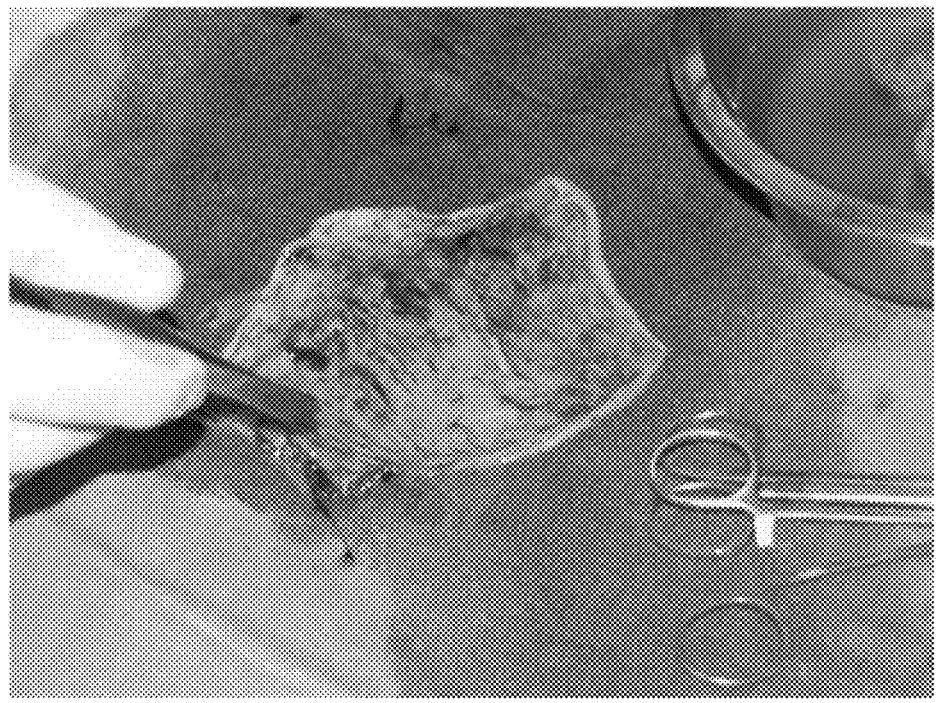
FIG. 11 depicts a placental membrane sheet.
Figure 12:
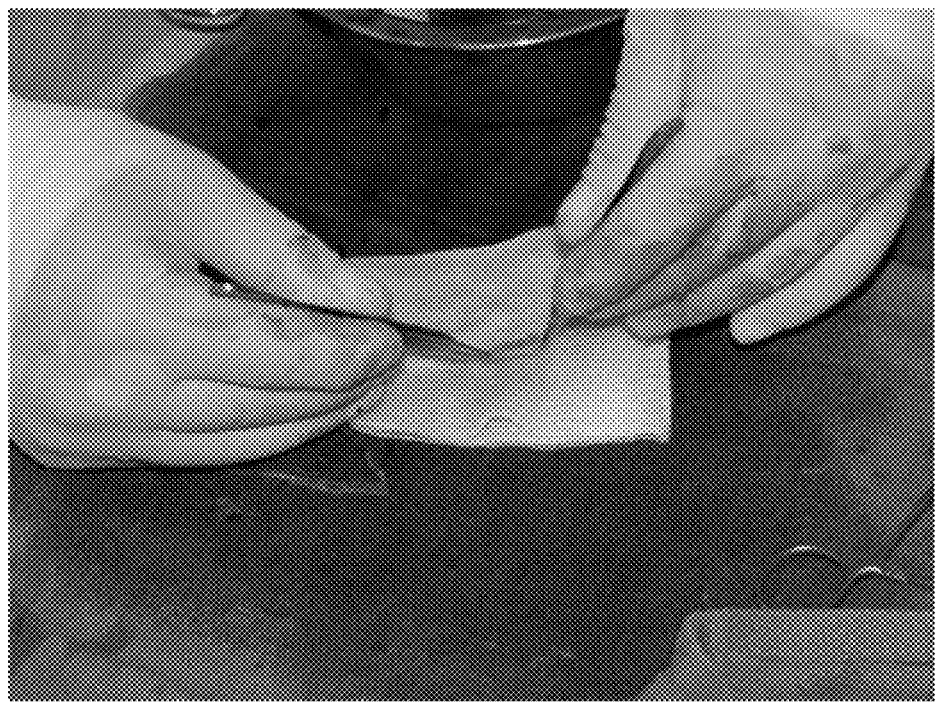
FIG. 12 depicts the preparation of an implantable placental membrane unit.
Figure 13:
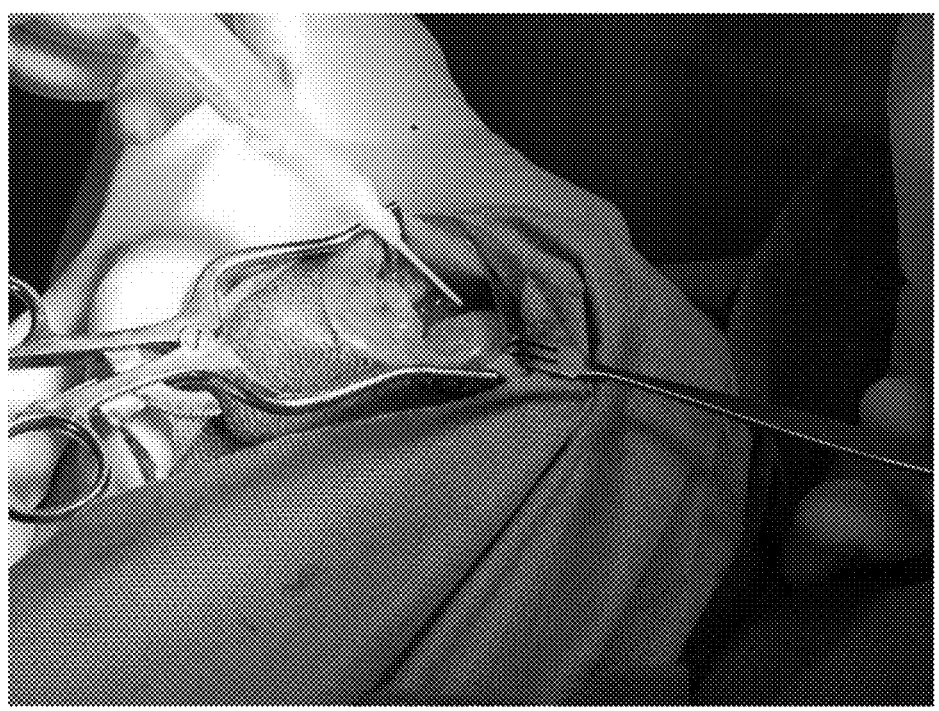
FIG. 13 depicts implantation of an implantable placental membrane unit into a sheep knee cartilage defect.

Method: Six adult sheep (less than three years old) where chosen for the study. Each sheep was anesthetized by a licensed veterinarian and one hind-quarter knee of each was sterilized and surgically exposed. As depicted in FIG. 10, two cartilage defects were created using curettes, one on the weight-bearing surface of the femoral condyle and one in the trochlear grove. The defects did not violate the subchondral bone. Three test sheep were used as control sheep and the cartilage defects were left unfilled. Three test sheep were chosen to receive human amniotic membrane implants. The amniotic membrane sheet was procured from a placenta and cut to fit the cartilage defect. As depicted in FIGS. 11 and 12, the membrane was folded into an implantable unit and arranged so that the cellular or epithelial layer faced the cartilage defect and the joint. Between the layers of the amnion membrane sheet, a small amount of demineralized bone was placed on a chorion side of the sheet. As depicted in FIG. 13, the amnion membrane implants were fixed to the cartilage defects on the femoral chondyles using micro bone anchors and fibrin glue. The amnion membrane implants were fixed to the trochlear defects using fibrin glue alone. The wounds were closed and the sheep were allowed to weight bear as tolerated. At six-months the sheep were sacrificed and the knees were harvested. Histological evaluation was made of the defects.

Figure 14:
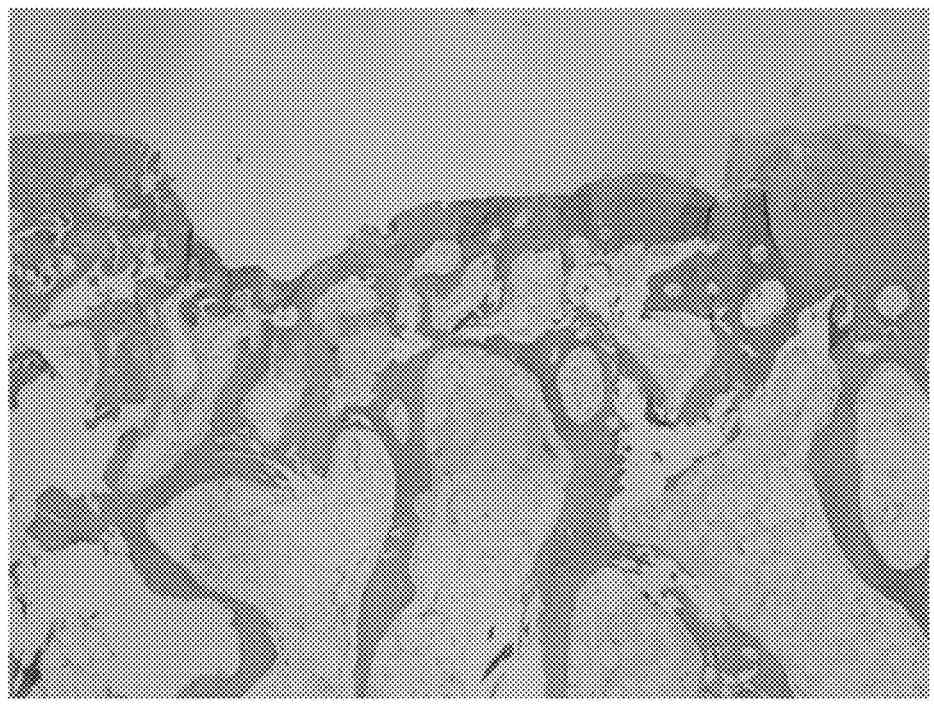
FIG. 14 is a low power histological view of a hematoxylin and eosin (HE) stained cartilage defect in a control sheep.
Figure 15:
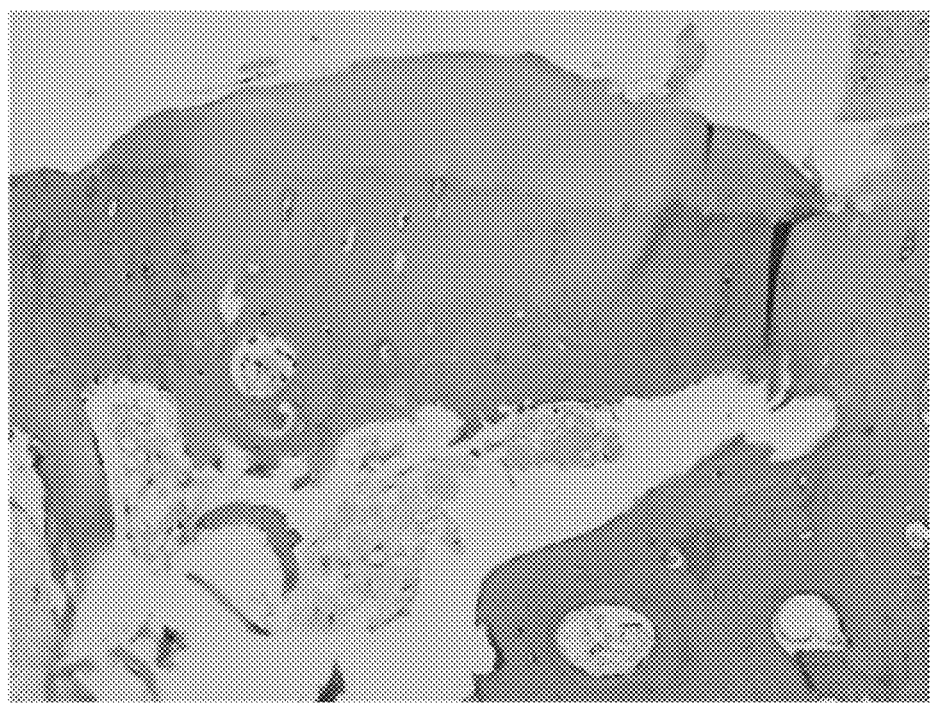
FIG. 15 is a high power histological view of a HE stained cartilage defect in a control sheep.
Figure 17:
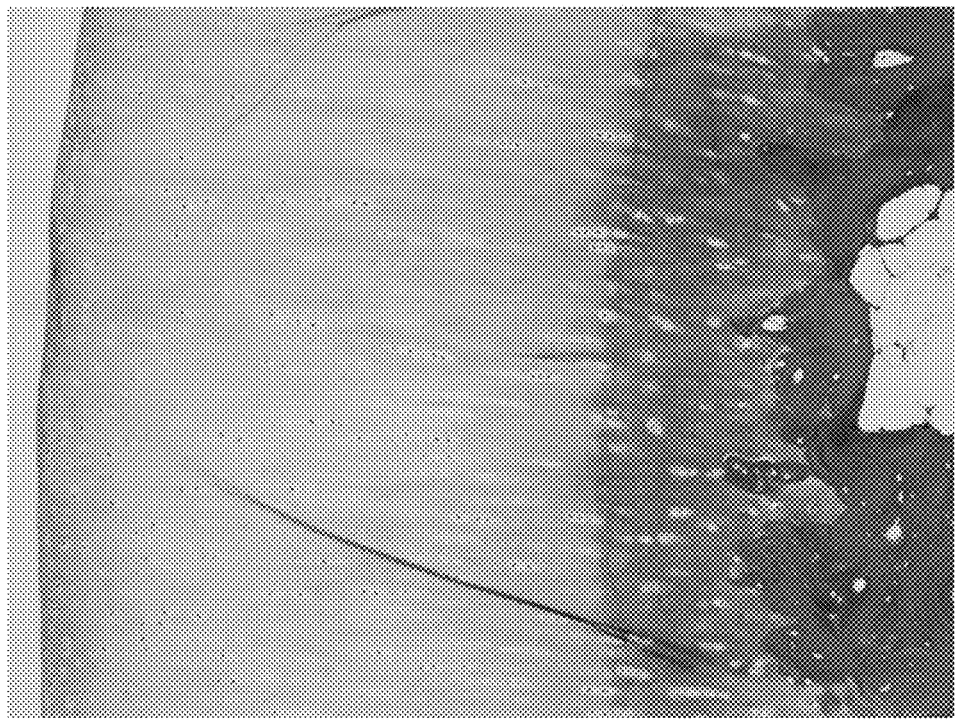
FIG. 17 is a low power histological view of a trichrome stained cartilage defect in a normal sheep.
Figure 16:
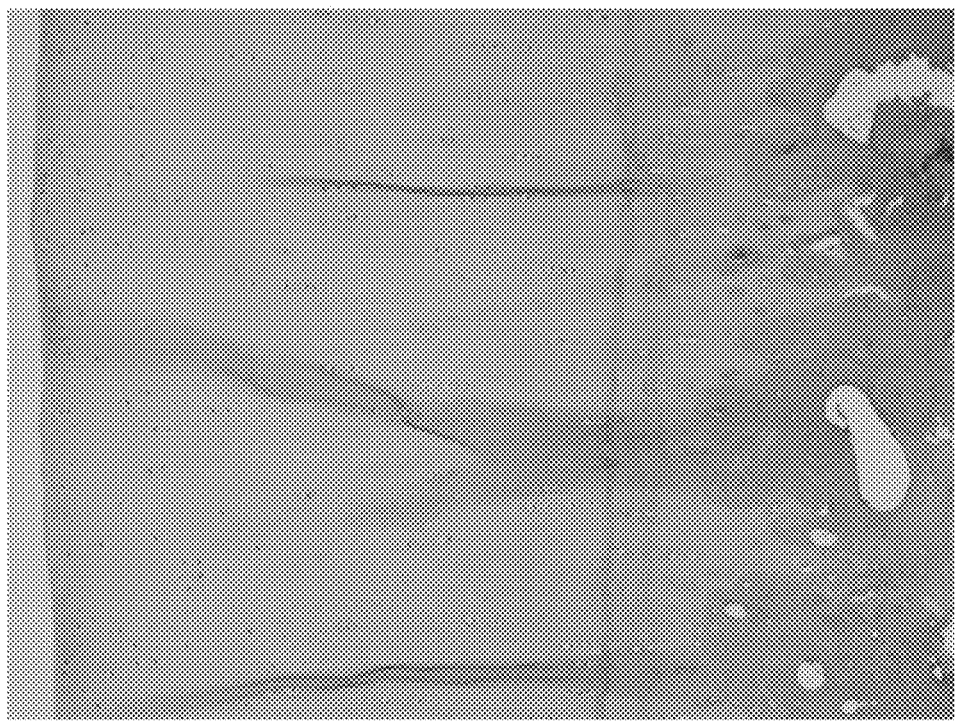
FIG. 16 is a low power histological view of a HE stained cartilage defect in a normal sheep.
Figure 18:
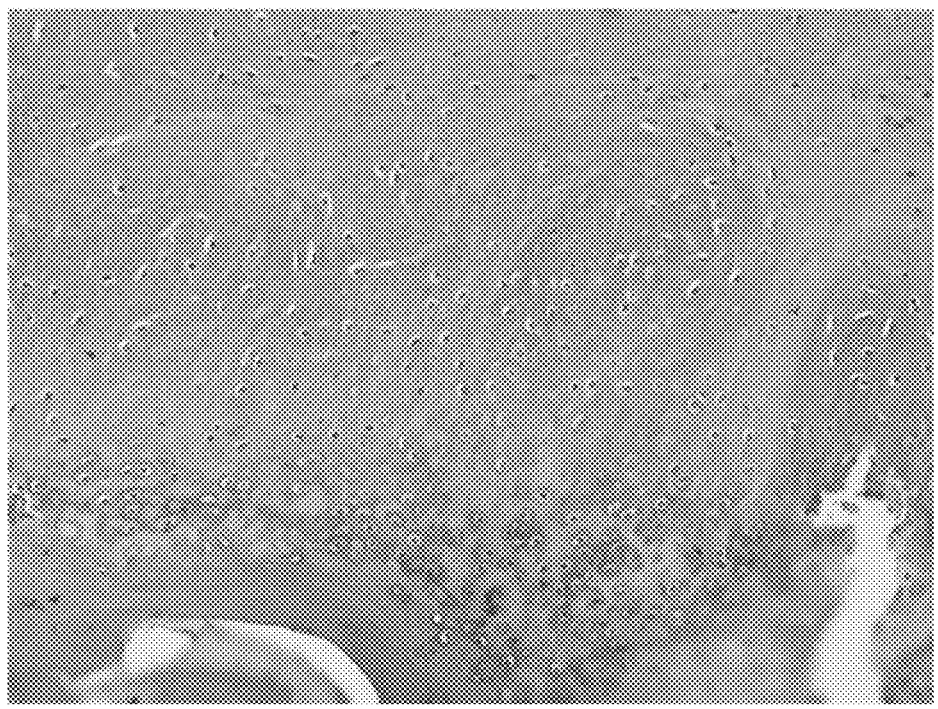
FIG. 18 is a high power histological view of an HE stained cartilage defect in a test sheep.
Figure 19:
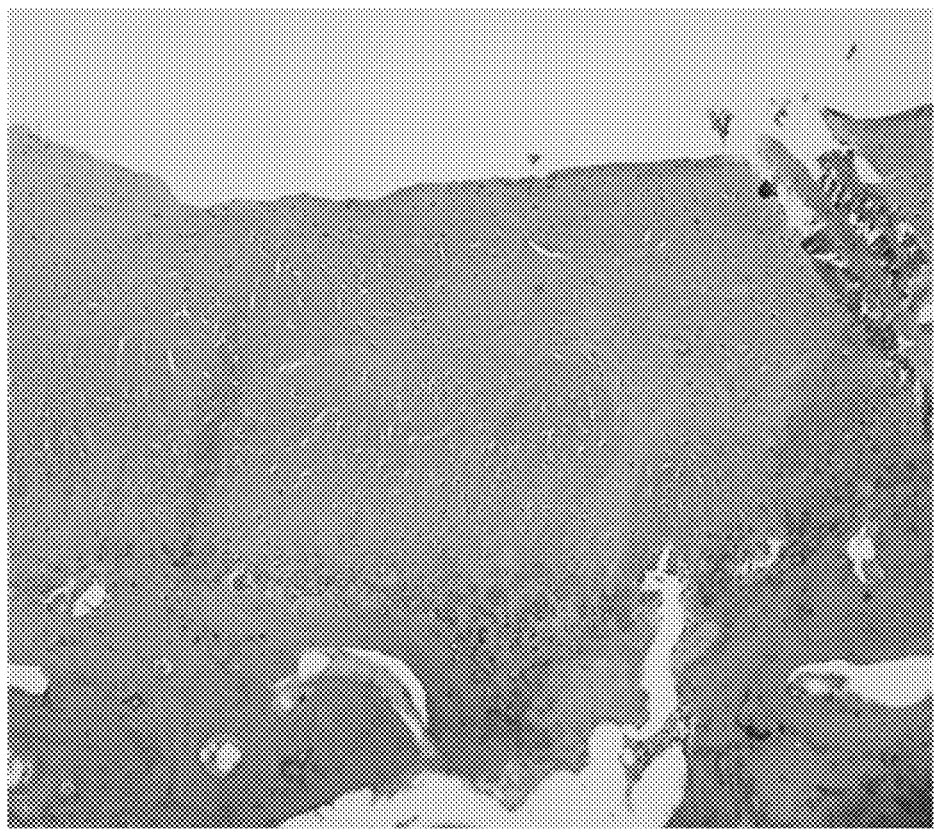
FIG. 19 is a low power histological view of an HE stained cartilage defect in a test sheep.
Figure 20:
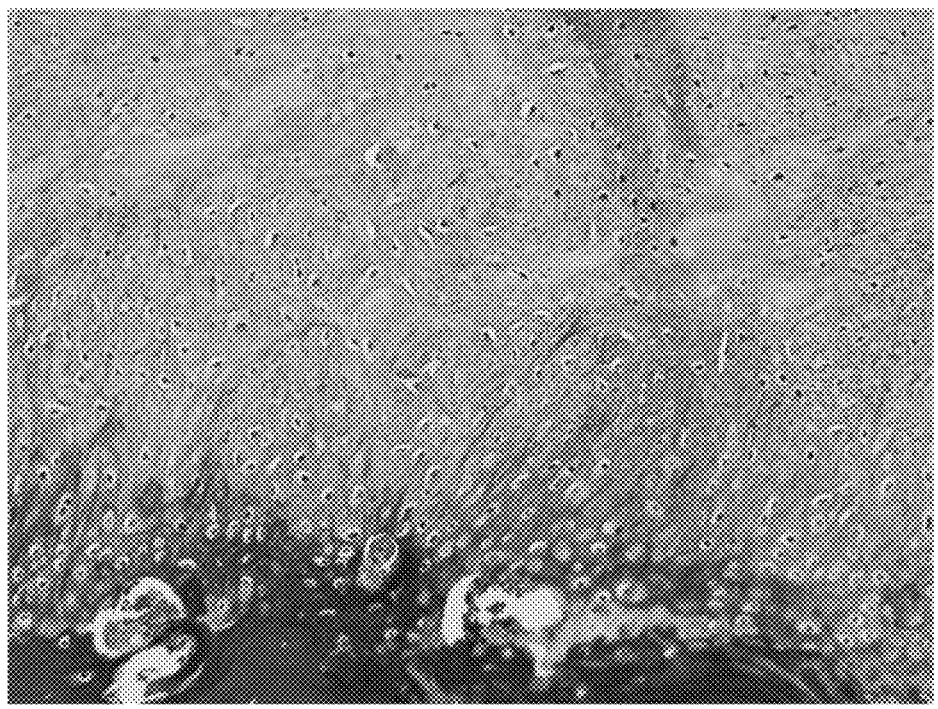
FIG. 20 is a high power histological view of an trichrome stained cartilage defect in a test sheep.
Figure 21:
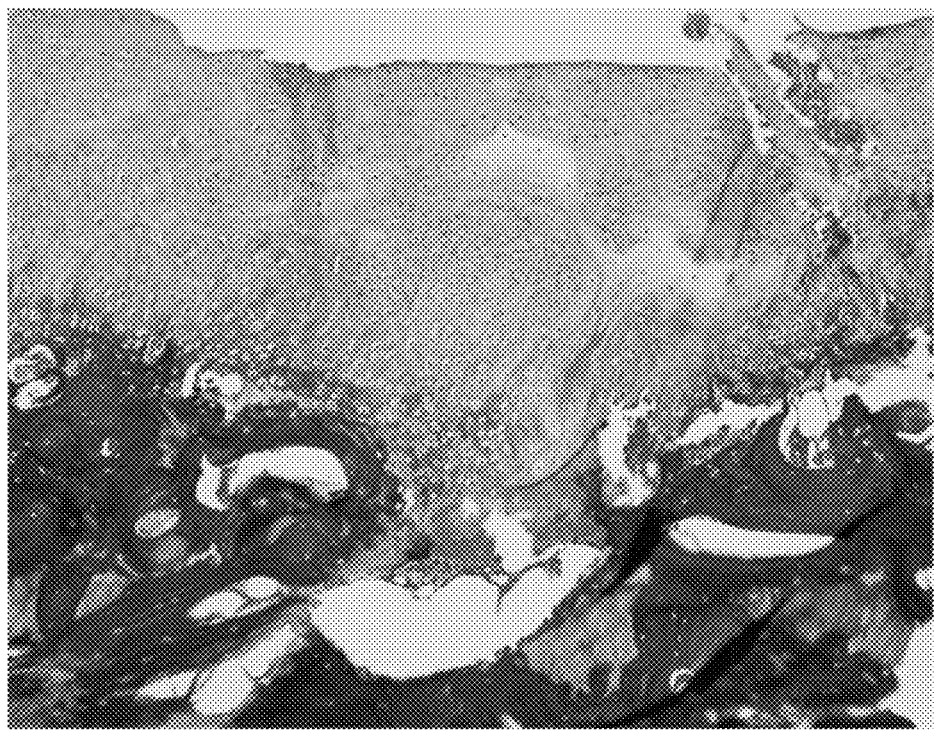
FIG. 21 is a low power histological view of an trichrome stained cartilage defect in a test sheep.

Results: Samples of the cartilage defects were examined histologically based on a simple, validated scoring system. The tests samples (depicted in FIGS. 18-21) were compared to the control samples (depicted in FIGS. 14 and 15) and the normal samples (depicted in FIGS. 16 and 17) taken from the sheep. Referring to the control sheep samples depicted in FIGS. 14 and 15, none of the cartilage defects in the control sheep filled in with hyaline cartilage or fibrocartilage. This is evident from the complete lack of tissue present in the voids created above the subchondral bone by the formation of the cartilage defects. The voids are represented in FIGS. 14 and 15 by the empty depressions defined by opposing vertically extending sidewalls which terminate at the upper ends thereof at the upper surface of the cartilage. In the test sheep in which the amnion membrane implants were placed, 50% of the defects appeared to retain the amnion membrane, which is consistent with other similar animal models. Referring to the test sheep samples depicted in FIGS. 18-21, the cartilage defects of the test sheep that retained their membranes had evidence of diffuse chondrocyte-like cell proliferation and showed a stromal matrix similar to hyaline cartilage. The graft samples of the test sheep defects showed 90% normal appearing cartilage compared with 40% normal in the control sheep. The grafts from the test sheep all scored a 3 on a 0-3 cartilage appearance scale compared with a 1.3 for the controls.

REFERENCES

1. Boo L, et al. A preliminary study of human amniotic membrane as a potential chondrocyte carrier, *Malay Orthop J* 3, 16-23 (2009).
2. Davis, J S, Skin transplantation with a review of 550 cases at the Johns Hopkins Hospital, *John Hopkins Med J* 15, 307 (1910).
3. Diaz-Prado S M, et al. Cell therapy and tissular engineering to regenerate articular cartilage, in BIOMEDICAL ENGINEERING, TRENDS, RESEARCH AND TECHNOLOGIES (Komorowska M A & Olsztynska-Janus S, eds.), pp. 193-216 (2011).
4. Diaz-Prado S M, et al. Potential use of the human amniotic membrane as a scaffold in human articular cartilage repair, *Cell Tissue Bank* 11, 183-195 (2010).
5. Hildner F, et al. State of the art and future perspectives of articular cartilage regeneration: a focus on adipose-derived stem cells and platelet-derived products, *J Tissue Eng Regen Med* 5, e36-e51 (2011).
6. Jin C Z, et al. Human amniotic membrane as a delivery matrix for articular cartilage repair, *Tiss Eng* 13, 693-702 (2007).
7. Kanthan S R, et al. The different preparations of human amniotic membrane (HAM) as a potential cell carrier for chondrocytes, *Eur Cell Mater* 20, 1 page (2010).
8. Krishnamurithy G, et al. Human amniotic membrane as a chondrocyte carrier vehicle/substrate: in vitro study, *J Biomed Mater Res Part A* 99A, 500-506 (2011).
9. Lindenmair A, et al. Osteogenic differentiation of intact human amniotic membrane, *Biomaterials* 31, 8659-8665 (2010).
10. Mermet I, et al. Use of amniotic membrane transplantation in the treatment of venous leg ulcers, *Wound Repair and Regeneration* 15, 459 (2007).
11. Moriya T, et al. Evaluation of reparative cartilage after autologous chondrocyte implantation for osteochondritis dissecans: histology, biochemistry, and MR imaging, *J Orthop Sci* 12, 265-273 (2007).
12. Niknejad H, et al. Properties of the amniotic membrane for potential use in tissue engineering, *Eur Cell Mater* 15, 88-99 (2008).
13. Wilshaw S P, et al. Production of an acellular amniotic membrane matrix for use in tissue engineering, *Tiss Eng* 12, 2117-2129 (2006).
14. Zhou S, et al. Demineralized bone promotes chondrocyte or osteoblast differentiation of human bone marrow stromal cells cultured in collagen sponges, *Cell Tissue Bank* 6, 33-44 (2005).
15. U.S. Pat. No. 7,824,711.
16. U.S. Pat. No. 6,063,094.
17. U.S. Pat. No. 5,612,028.
18. U.S. Pat. No. 5,004,468.
19. U.S. Pat. No. 3,640,279.
20. U.S. Pat. No. 3,472,228.
21. U.S. Pat. No. 3,358,688.
22. U.S. Patent Application Publication No. 2003-0187515.
23. U.S. Patent Application Publication No. 2004-0161419.

What is claimed is:

1. A method of generating cartilage in vivo in a skeletal joint comprising:
removing diseased cartilage from the skeletal joint thereby forming a void and exposing a subchondral bone, implanting a placental membrane preparation into the void of the skeletal joint wherein the placental membrane preparation comprises an intact placental membrane sheet and a demineralized bone powder (DBP) applied thereto, and generating chondrocytes within the void of the skeletal joint via differentiation of viable mesenchymal stem cells that are native to and have not been isolated from the intact placental membrane sheet without differentiation of the mesenchymal stem cells into osteoblasts.

2. The method according to claim 1 wherein the intact placental membrane sheet excludes a chorion.

3. The method according to claim 1 further comprising directly contacting an epithelial cell layer of an amnion side of the intact placental membrane sheet to the skeletal joint.

4. The method according to claim 1 further comprising directly contacting an epithelial cell layer of an amnion side of the intact placental membrane sheet to the skeletal joint without directly contacting a chorion side of the intact placental membrane sheet to the skeletal joint.

5. The method according to claim 1 wherein the preparation is essentially free of chondrocytes when implanted into the skeletal joint.

6. The method according to claim 1 further comprising implanting the preparation into the skeletal joint no more than 6 hours after the DBP is applied to the placental membrane sheet.

7. The method according to claim 1 further comprising generating chondrocytes within the intact placental membrane sheet via differentiation of the mesenchymal stem cells that are native to the intact placental membrane sheet and in the absence of growth factors derived from sources other than the intact placental membrane sheet and the DBP.

8. The method according to claim 1 further comprising generating hyaline articular cartilage within the skeletal joint from the preparation via differentiation of the mesenchymal stem cells that are native to the intact placental membrane sheet with no fibrocartilage generation.

9. The method according to claim 1 wherein, prior to implantation, the intact placental membrane sheet is arranged in a manner so that only an epithelial layer of cells of the intact placental membrane sheet directly contacts the skeletal joint when implanted therein.

10. The method according to claim 1 wherein the placental membrane preparation includes a plurality of stacked placental membrane sheets, wherein the placental membrane sheets of the plurality of stacked placental membrane sheets are separate sheets.

11. A method of generating cartilage in vivo in a skeletal joint comprising, removing a diseased cartilage portion from a cartilage body of the skeletal joint thereby forming a void, providing an implant that includes a placental membrane sheet having an epithelial monolayer and viable mesenchymal stem cells that are native to the placental membrane sheet, the mesenchymal stem cells being separated from the epithelial monolayer by a basement membrane of the placental membrane sheet, arranging the implant to present with an exterior surface portion having an upper surface displaying the epithelial monolayer and a lower surface portion displaying the epithelial monolayer, placing the implant into the void, wherein the void is defined by a sidewall, a bottom, and an upper opening, and reducing differentiation of the mesenchymal stem cells into osteoblasts by arranging the implant within the void so that the lower surface portion contacts the bottom and the upper surface portion faces the upper opening.

12. The method according to claim 11 wherein bleeding is minimized during the removal of the diseased cartilage.

13. The method according to claim 11 wherein bleeding is minimized in part by the application of a hemostatic agent.

14. The method according to claim 11 wherein the bleeding is minimized in part by the avoidance of abrasions to the subchondral bone and calcified cartilage.

15. The method according to claim 11 wherein the removal of healthy cartilage is minimized during the removal of the diseased cartilage.

16. The method according to claim 11 wherein the placental membrane sheet includes a chorion layer impregnated with demineralized bone powder.

17. The method according to claim 16 wherein the chorion layer of the placental membrane sheet includes a viable stromal cell layer.

18. The method according to claim 11 wherein the placental membrane sheet includes a demineralized bone powder.

19. The method according to claim 14 wherein the implant is essentially free of chondrocytes at the moment when placed into the void.

20. The method according to claim 14 wherein the implant is free of osteoblasts at the moment when placed into the void.

21. The method according to claim 14 wherein the implant is free of osteoblasts six months after placement into the void.

22. The method according to claim 14 wherein a majority of the mesenchymal stem cells differentiate into hyaline cartilage cells following placement of the implant into the void.

23. A method of generating cartilage in vivo in a skeletal joint comprising:
inserting a demineralized bone powder-impregnated first intact placental membrane sheet into a void formed in a cartilage body of a skeletal joint, the void containing bone marrow, and generating chondrocytes within the cartilage body via differentiation of viable mesenchymal stem cells that are native to and have not been isolated from the first intact placental membrane sheet without differentiation of the mesenchymal stem cells that are native to the first intact placental membrane sheet into osteoblasts.

24. The method according to claim 23 further comprising folding the first intact placental membrane sheet.

25. The method according to claim 23 further comprising stacking additional placental membrane sheets on the first intact placental membrane sheet.

26. The method according to claim 23 further comprising, prior to inserting the first intact placental membrane sheet into the void, forming an implant from the first intact placental membrane sheet, the implant having an interior portion that is separated from an exterior surface of the implant by a basement membrane, wherein the mesenchymal stems cells are located in the interior portion.

27. The method according to claim 26 further comprising preventing leakage of the bone marrow into the interior portion by arranging the exterior surface to be between the bone marrow and the interior portion.

\* \* \* \* \*